(12) United States Patent
Hausen

(10) Patent No.: US 8,695,864 B1
(45) Date of Patent: Apr. 15, 2014

(54) MAGNETIC COUPLING FOR SURGICAL STAPLER

(75) Inventor: Bernard A. Hausen, Redwood City, CA (US)

(73) Assignee: Cardica, Inc., Redwood City, CA (US)

( * ) Notice: Subject to any disclaimer, the term of this patent is extended or adjusted under 35 U.S.C. 154(b) by 0 days.

(21) Appl. No.: 13/185,679

(22) Filed: Jul. 19, 2011

Related U.S. Application Data

(60) Provisional application No. 61/365,710, filed on Jul. 19, 2010.

(51) Int. Cl.
*A61B 17/068* (2006.01)

(52) U.S. Cl.
USPC ............... 227/175.1; 227/19; 227/179.1

(58) Field of Classification Search
USPC ...................... 227/175.1, 19, 179.1
See application file for complete search history.

(56) References Cited

U.S. PATENT DOCUMENTS

| | | | | |
|---|---|---|---|---|
| 5,205,459 A | * | 4/1993 | Brinkerhoff et al. | 227/179.1 |
| 5,271,544 A | * | 12/1993 | Fox et al. | 227/180.1 |
| 5,275,322 A | * | 1/1994 | Brinkerhoff et al. | 227/175.1 |
| 5,285,945 A | * | 2/1994 | Brinkerhoff et al. | 227/179.1 |
| 5,292,053 A | * | 3/1994 | Bilotti et al. | 227/179.1 |
| 5,333,773 A | * | 8/1994 | Main et al. | 227/179.1 |
| 5,350,104 A | * | 9/1994 | Main et al. | 227/179.1 |
| 5,533,661 A | * | 7/1996 | Main et al. | 227/176.1 |
| 7,371,243 B1 | * | 5/2008 | Nielsen et al. | 606/142 |

* cited by examiner

*Primary Examiner* — Brian D Nash
(74) *Attorney, Agent, or Firm* — Cardica, Inc.

(57) ABSTRACT

A surgical tool may include a circular surgical stapler and an anvil initially disconnected and separate from the surgical stapler; where at least one of the circular surgical stapler and the anvil is magnetic.

10 Claims, 3 Drawing Sheets

MAGNETIC COUPLING FOR SURGICAL STAPLER

This application claims priority to U.S. Provisional Patent Application Ser. No. 61/365,710, filed on Jul. 19, 2010, which is herein incorporated by reference in its entirety.

FIELD OF THE INVENTION

The invention generally relates to surgical staplers and stapling, and more particularly to circular surgical staplers.

BACKGROUND

Referring to FIG. 1, a conventional circular stapler 2 includes a stapler 4 that is initially separate and disconnected from an anvil 6. A first piercing coupling element 8 extends from the stapler 4, and a second piercing coupling element 10 extends from the anvil 6. The surgeon creates an opening 12 in each segment of the intestine 14a, 14b, and each piercing coupling element 8, 10 is inserted through the corresponding opening. The piercing coupling elements 8, 10 are then connected to allow the stapler 4 and anvil 6 to connect the segments of the intestine 14a, 14b. A disadvantage of the conventional surgical stapler 2 is the need to create openings 12 in the segments of the intestine 14a, 14b prior to connecting the segments 14a, 14b together, which allows bacteria from the intestinal tract to enter the thoracic cavity. Further, the piercing coupling elements 8 add length, size and weight to the conventional surgical stapler.

BRIEF DESCRIPTION OF THE DRAWINGS

The use of the same reference symbols in different figures indicates similar or identical items.

DETAILED DESCRIPTION

Figure 1:
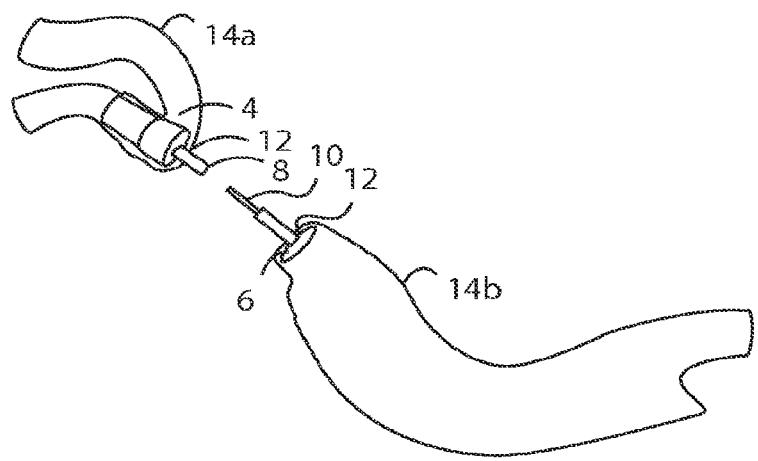
FIG. 1 is a perspective view of a conventional prior art circular surgical stapler.
Figure 2:
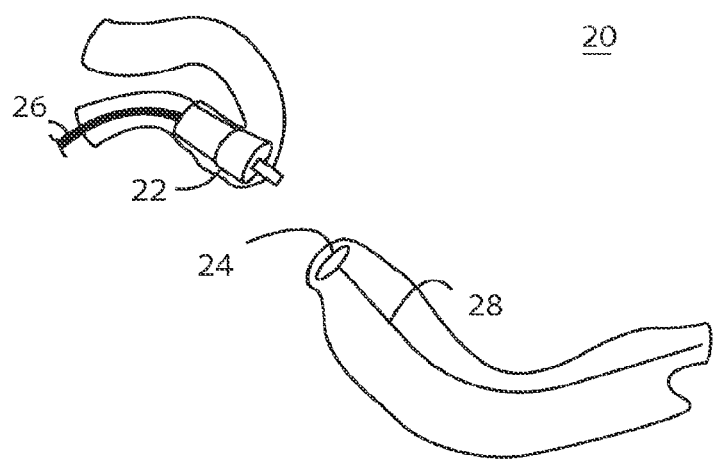
FIG. 2 is a perspective view of a circular stapler including a stapler and an anvil, at least one of which is magnetic, placed in two segments of an intestine.

Referring to FIG. 2, a circular stapler 20 may include a stapler 22 that is initially separate and disconnected from an anvil 24. A first guidewire 26 or other control structure may extend from the stapler 22, and a second guidewire 28 or other control structure may extend from the anvil 24. One or both of the stapler 22 and anvil 24 may be magnetic. That is, one or both of the stapler 22 and anvil 24 may emit a magnetic field. The stapler 22 and/or anvil 24 may be passively magnetic or actively magnetic. "Passively magnetic" means that the stapler 22 and/or anvil 24 is fabricated from a material that is magnetized, such that the stapler 22 and/or anvil 24 emits a magnetic field without the need for application of energy thereto. "Actively magnetic" means that the stapler 22 or anvil 24 is fabricated from a material that is not magnetized, such that the stapler 22 and/or anvil 24 emits a magnetic field only upon the application of energy thereto. Where the stapler 22 and/or anvil 24 is actively magnetic, the actively magnetic components may include an electromagnet, solenoid or other such mechanism that emits a magnetic field upon application of energy thereto. Where only one of the stapler 22 and anvil 24 is magnetic, the other is made from a ferrous or other material that is susceptible to a magnetic field, such that moving the stapler 22 and anvil 24 into proximity causes the component that is magnetic to attract the other component to it.

Figure 3:
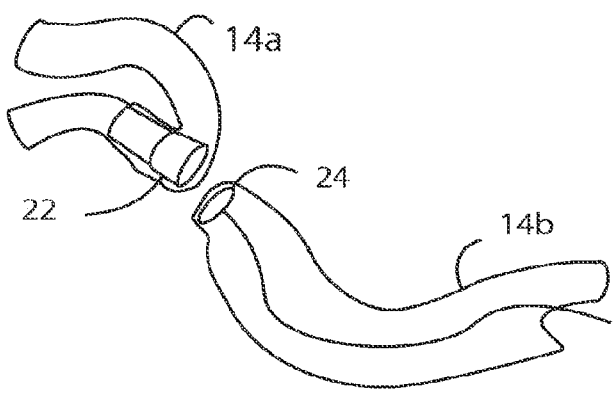
FIG. 3 is a perspective view of the circular stapler of FIG. 2, where the two segments are in proximity to one another.

Referring also to FIG. 3, the stapler 22 is inserted into a first segment 14a of the intestine or other tissue. The anvil 24 is inserted into a second segment 14b of the intestine or other tissue. The insertion of the stapler 22 and anvil 24 into tissue 14 is accomplished in a conventional manner known to those skilled in the art, or may be performed in any other suitable manner. The segments 14a, 14b may initially be spaced apart from another, and are brought into proximity to one another in a conventional manner or any other suitable manner. As seen in FIG. 3, the stapler 22 and anvil 24 are brought into proximity with one another.

Figure 4:
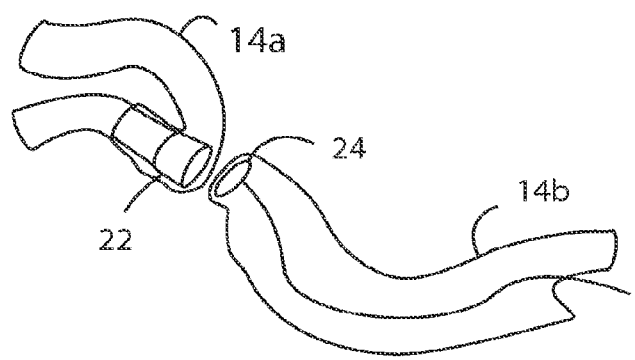
FIG. 4 is a perspective view of the circular stapler of FIG. 2 where the stapler and anvil are aligned with one another.

Referring to FIG. 4, the stapler 22 and anvil 24 self-align with one another as they are brought into proximity. If the stapler 22 and/or anvil 24 are actively magnetic, then before or after they are brought into proximity with one another, energy is transmitted to the stapler 22 and/or anvil 24 to cause the stapler 22 and/or anvil 24 to emit a magnetic field. The stapler 22 and/or anvil 24 are magnetic, as set forth above, and if either component is not magnetic it is susceptible to magnetism. As a result, when the stapler 22 and anvil 24 are brought into proximity, the effect of the magnetic field emitted by one or both of the stapler 22 and anvil 24 pulls the stapler 22 and anvil 24 together and causes them to self-align with one another. Intact tissue of the intestine 14 is then present between the stapler 22 and anvil 24, such that the two segments 14a, 14b of the intestine are held together without a break or opening in the tissue of either segment 14a, 14b of the intestine.

Figure 5:
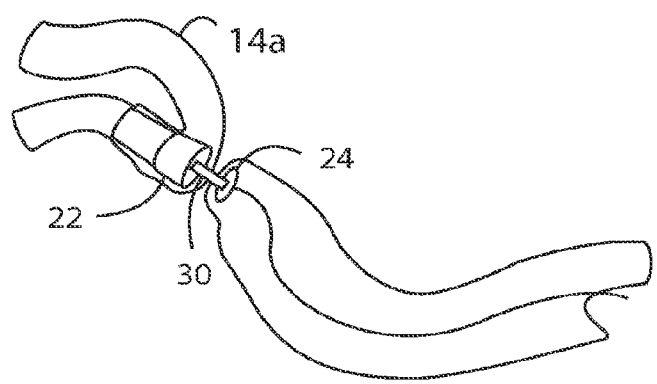
FIG. 5 is a perspective view of the circular stapler of FIG. 2, where a piercing fastener has been extended from the stapler into engagement with the anvil.
Figure 6:
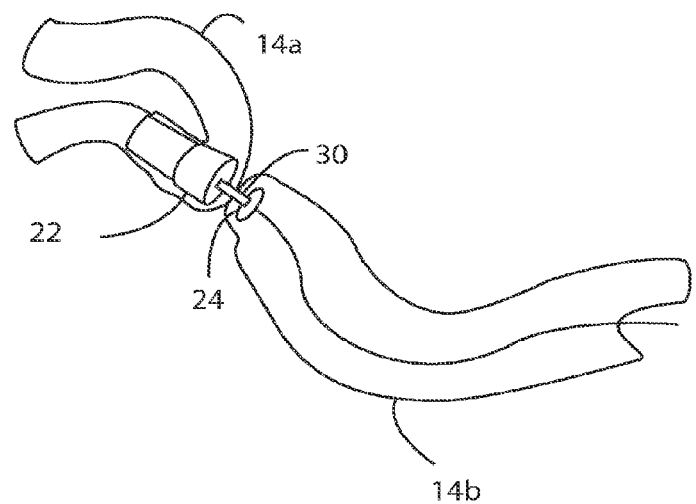
FIG. 6 is a perspective view of the circular stapler of FIG. 5, where the tissue between the stapler and anvil has been compressed.
Figure 7:
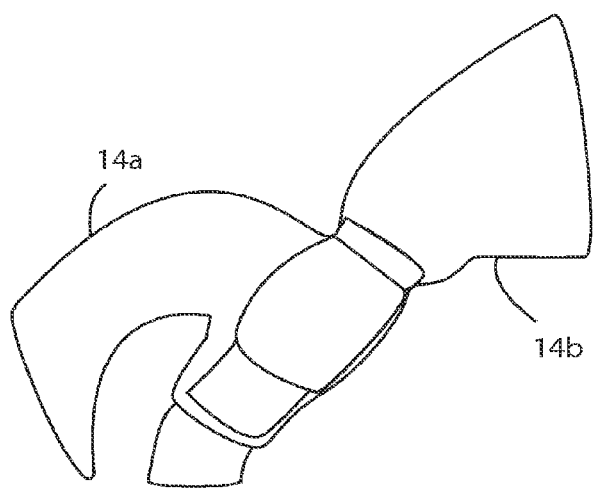
FIG. 7 is a perspective view of a completed connection between segments of an intestine.

Referring also to FIG. 5, a piercing fastener 30 may then be extended from the anvil 24 toward the stapler 22. The fastener 30 may be sharp, threaded, or configured in any suitable manner. As one example, the fastener 30 may be a pointed and threaded screw. As another example, the piercing fastener 30 may be extended from the stapler 22 toward the anvil 24. As another example, a piercing fastener 30 may be extended from each of the stapler 22 and the anvil 24 toward the other. As the piercing fastener 30 is extended, it penetrates each segment 14a, 14b of the intestine and is received in and held by the stapler 22. Referring also to FIG. 6, the piercing fastener 30 may be rotated or otherwise advanced to bring the stapler 22 and anvil 24 closer to one another and compress the tissue of the segments 14a, 14b of the intestine that is positioned and held between the stapler 22 and the anvil 24. The stapler 22 is then actuated, such as by the guidewire 26, to deploy one or more staples toward the anvil 24 through the tissue of the segments 14a, 14b of the intestine held between the stapler 22 and anvil 24. The segments 14a, 14b are thereby connected together. A cutter may then be advanced from the stapler 22 toward the anvil 24 in order to cut an opening through the segments 14a, 14b of the intestine held between the stapler 22 and anvil 24. Alternately, the cutter may be advanced from the anvil 24 toward the stapler 22. Advantageously, the stapler 22 deploys a plurality of staples in a circular or other closed pattern, and the cutter cuts an opening through the stapled segments 14a, 14b of the intestine within the perimeter defined by the staples in tissue.

The piercing fastener 30 is then disengaged from the stapler 22 and retracted toward the anvil 24. If the stapler 22 and/or anvil 24 are actively magnetic, the application of energy to the stapler 22 and/or anvil 24 is ceased. The stapler 22 and anvil 24 are then moved away from one another, such as by applying force to the guidewire 26 attached to the stapler 22 and the guidewire 28 attached to the anvil 24. The intestinal segments 14a, 14b are securely connected, and the procedure is complete.

While the invention has been described in detail, it will be apparent to one skilled in the art that various changes and modifications can be made and equivalents employed, without departing from the present invention. It is to be understood that the invention is not limited to the details of construction, the arrangements of components, and/or the method set forth in the above description or illustrated in the drawings. Statements in the abstract of this document, and any summary statements in this document, are merely exemplary; they are not, and cannot be interpreted as, limiting the scope of the claims. Further, the figures are merely exemplary and not limiting. Topical headings and subheadings are for the convenience of the reader only. They should not and cannot be construed to have any substantive significance, meaning or interpretation, and should not and cannot be deemed to indicate that all of the information relating to any particular topic is to be found under or limited to any particular heading or subheading. Therefore, the invention is not to be restricted or limited except in accordance with the following claims and their legal equivalents.

What is claimed is:

1. A surgical tool, comprising:
    a cylindrical surgical stapler having a first circular end and a second circular end;
    an anvil initially disconnected and separate from said surgical stapler,
    wherein at least one of said cylindrical surgical stapler and said anvil comprise a magnetic a material; and
    a cutter extending from one of the surgical stapler or the anvil, wherein the cutter is operable to cut an opening through segments disposed between the surgical stapler and the anvil when one of the first circular end or the second circular end of the surgical stapler is proximate to the anvil, wherein the cylindrical surgical stapler and the anvil self-align with one another when disposed in different tubular structures via a magnetic field of the magnetic material prior to cutting the opening through the segments of the different tubular structures.

2. The surgical tool of claim 1, wherein the anvil has a circular surface.

3. The surgical tool of claim 1, further comprising:
    a piercing fastener extending from one of the surgical stapler or the anvil.

4. The surgical tool of claim 1, wherein the surgical stapler is operable to deploy a plurality of staples in a circular pattern.

5. The surgical tool of claim 1, wherein the surgical stapler is actuated through a guidewire.

6. A surgical tool, comprising:
    a surgical stapler having a first circular end and a second circular end, the surgical stapler is operable to deploy a plurality of staples in a circular pattern;
    an anvil initially disconnected and separate from said surgical stapler, wherein at least one of the circular surgical stapler and the anvil comprise a magnetic a material; and
    a cutter extending from one of the surgical stapler or the anvil, wherein the cutter is operable to cut an opening through segments disposed between the surgical stapler and the anvil when one of the first circular end or the second circular end of the surgical stapler is proximate to a surface of the anvil, wherein the cylindrical surgical stapler and the anvil self-align with one another when disposed in different tubular structures via a magnetic field of the magnetic material prior to cutting the opening through the segments of the different tubular structures.

7. The surgical tool of claim 6, wherein the surface of the anvil is circular.

8. The surgical tool of claim 6, further comprising:
    a piercing fastener extending from one of the surgical stapler or the anvil.

9. The surgical tool of claim 6, wherein the surgical stapler is operable to deploy a plurality of staples in a circular pattern.

10. The surgical tool of claim 6, wherein the surgical stapler is actuated through a guidewire.

* * * * *